United States Patent
Mjalli et al.

(10) Patent No.: US 9,855,251 B2
(45) Date of Patent: Jan. 2, 2018

(54) USE OF METFORMIN IN COMBINATION WITH A GLUCOKINASE ACTIVATOR AND COMPOSITIONS COMPRISING METFORMIN AND A GLUCOKINASE ACTIVATOR

(71) Applicant: vTv Therapeutics LLC, High Point, NC (US)

(72) Inventors: Adnan M. M. Mjalli, Oak Ridge, NC (US); Maria Carmen Valcarce Lopez, Oak Ridge, NC (US)

(73) Assignee: vTv Therapeutics LLC, High Point, NC (US)

( * ) Notice: Subject to any disclaimer, the term of this patent is extended or adjusted under 35 U.S.C. 154(b) by 0 days.

(21) Appl. No.: 14/988,143

(22) Filed: Feb. 11, 2016

(65) Prior Publication Data

US 2016/0184277 A1 Jun. 30, 2016

Related U.S. Application Data

(62) Division of application No. 13/114,964, filed on May 24, 2011, now Pat. No. 9,359,313.

(60) Provisional application No. 61/348,554, filed on May 26, 2010.

(51) Int. Cl.
*A61K 31/425* (2006.01)
*A61K 31/155* (2006.01)
*A61K 31/426* (2006.01)
*C07D 277/54* (2006.01)

(52) U.S. Cl.
CPC .......... *A61K 31/426* (2013.01); *A61K 31/155* (2013.01); *C07D 277/54* (2013.01)

(58) Field of Classification Search
None
See application file for complete search history.

(56) References Cited

U.S. PATENT DOCUMENTS

| | | | | |
|---|---|---|---|---|
| 3,957,853 | A | 5/1976 | Bohuon | |
| 9,359,313 | B2 * | 6/2016 | Mjalli | C07D 277/54 |
| 2007/0054897 | A1 * | 3/2007 | Murray | A61K 31/4168 514/218 |
| 2008/0319028 | A1 * | 12/2008 | Murray | C07C 275/62 514/353 |
| 2009/0105482 | A1 * | 4/2009 | Lau | C07D 277/48 548/140 |
| 2009/0118501 | A1 * | 5/2009 | Murray | C07D 277/48 544/130 |
| 2012/0071404 | A1 * | 3/2012 | Tucker | A61K 38/24 514/7.7 |
| 2014/0066372 | A1 | 3/2014 | Valcarce Lopez et al. | |
| 2016/0015638 | A1 | 1/2016 | Mo et al. | |
| 2016/0015816 | A1 | 1/2016 | Benjamin et al. | |

FOREIGN PATENT DOCUMENTS

| | | | |
|---|---|---|---|
| CA | 2724116 | 11/2009 | |
| CA | 2724116 A1 * | 11/2009 | .......... C07D 231/56 |
| DE | 2357875 | 9/1974 | |
| WO | WO 2005/023766 | 3/2005 | |
| WO | WO 2005/066145 | 7/2005 | |
| WO | WO 2005066145 A1 * | 7/2005 | ......... A61K 31/4168 |
| WO | WO 2004/002481 | 1/2007 | |
| WO | WO 2007/006760 | 1/2007 | |
| WO | WO 2008/084043 | 7/2008 | |
| WO | WO 2011/025270 | 3/2011 | |
| WO | WO 2013/173417 | 11/2013 | |
| WO | WO 2014/137797 | 9/2014 | |
| WO | WO 2014/137799 | 9/2014 | |

OTHER PUBLICATIONS

McVean, M. et al., "Combination Therapy of ARRY-403 with Metformin, Sitagliptin or Pioglitazone Results in Additive Glucose Lowering in Female ZDF Rats," Poster 104—Keystone Symposium: Type 2 Diabetes and Insulin Resistance (J3), Jan. 20-25, 2009, Banff, AB (Array Biopharma).*
U.S. Appl. No. 14/071,976, filed Nov. 2013, Valcarce Lopez.*
Aicher et al., "ARRY-403, A Novel Glucokinase Activator with Potent Glucose-Dependent Anti-Hyperglycemic Activity . . . Mellitus," Poster 126—Keystone Symposium: Type 2 Diabetes and Insulin Resistance (J3), Jan. 20-25, 2009, Banff, AB (Array Biopharma).
Amendment No. 6 to Form S-1 Registration Statement for vTv Therapeutics Inc., Jul. 24, 2015. pp. 2-3, 84, 96-99.
Database WPI Week 201123, Thomson Scientific, London, GB; An 2011-C11325 & WO 2011/025270 A2 (Hanall Biopharma Co Ltd) Mar. 3, 2011 (Mar. 3, 2011).
European Patent Office Search Report for related EP Application No. 11787250.7, dated Jan. 30, 2014.
Guidance for Industry, Estimating the Maximum Safe Starting Does in Initial Clinical Trials for Therapeutics in Adult Healthy Volunteers, FDA, Jul. 2005.
International Search Report for related International Application No. PCT/US2011/037752, mailed Aug. 22, 2011.
Investor Presentation—Jul. 2015. Slides 19-23.
McVean et al., "Combination Therapy of ARRY-403 with Metformin, Sitagliptin or Pioglitazone Results in Additive Glucose Lowering in Female ZDF Rats," Poster 104—Keystone Symposium: Type 2 Diabetes and Insulin Resistance (J3), Jan. 20-25, 2009, Banff, AB (Array Biopharma).
Valcarce, C. and Fong, T.—TTP399, A Liver Selective Glucokinase Activator Increases Efficacy of Currently Marketed Therapies for Type 2 Diabetes. Jun. 2015. ADA 75th Scientific Sessions, Boston.

(Continued)

Primary Examiner — Svetlana M Ivanova
(74) Attorney, Agent, or Firm — Samuel B. Rollins

(57) ABSTRACT

The present invention provides uses of a glucokinase activator in combination with metformin. Uses include treating type 2 diabetes, lowering blood glucose, improving insulin sensitivity, enhancing phosphorylation of glucose, and improving the therapeutic effectiveness of metformin. The invention also provides pharmaceutical compositions that comprise a GK activator and metformin. The invention also provides a salt formed between metformin and a GK activator.

16 Claims, 1 Drawing Sheet

(56) References Cited

OTHER PUBLICATIONS

Valcarce, C. and Fong, T. Abstract—TTP399, A Liver Selective Glucokinase Activator Increases Efficacy of Currently Marketed Therapies for Type 2 Diabetes. Jun. 2015. ADA 75th Scientific Sessions, Boston.
Valcarce, C., Attucks, O., Fong, T., Freeman, J.—TTP399, A Liver Selective Glucokinase Activator (GKA) the Preserves the Physiological Regulation of Glucokinase (GK) by GK Reaulatory Protein (GKRP). Jun. 2015. ADA 75th Scientific Sessions, Boston.
Valcarce, C., Attucks, O., Fong, T., Freeman, J. Abstract—TTP399, A Liver Selective Glucokinase Activator (GKA) the Preserves the Physiological Regulation of GluCokinaSe (GK) by GK Regulatory Protein (GKRP). Jun. 2015. ADA 75th Scientific Sessions, Boston.
Valcarce, C., Grimes, I., Gustavson; S., Burstein, A., Mjalli, A. Abstract—TTP399, a Liver-Selective Glucose Kinase Activator (GKA), Lowers Glucose and Does Not Increase Lipids in Subjects with Type 2 Diabetes Mellitus (T2DM). Jun. 2014. ADA 74th Scientific Sessions.
Valcarce, C., Grimes, I., Gustavson, S., Burstein, A., Mjalli, A. TTP399, a Liver-Selective Glucose Kinase Activator (GKA), Lowers Glucose and Does Not increase Lipids in Subjects with Type 2 Diabetes Mellitus (T2DM). Jun. 2014. ADA 74th Scientific Sessions.
Written Opinion for related International Application No. PCT/US2011/037752, mailed Aug. 22, 2011.
Carmen Valcarce "The Importance of Tissue Selectivity and Preservation of the Physiological Regulation when Targeting Key Metabolic Regulators as Glucokinase," Poster presented at the Keystone Conference in La Jolla, CA, Apr. 17-20, 2016.
Eiki et al., "Pharmacokinetic and Pharmacodynamic Properties of the Glucokinase Activator MK-0941 in Rodent Models of Type 2 Diabetes and Healthy Dogs," Molecular Pharmacology 80:1156-1165 (2011).
Ericsson et al., "The glycokinase activator AZD6370 decreases fasting and posprandial glucose in type 2 diabetes mellitus patients with effects influenced by dosing regimen and food," Diabetes Research and Clinical Practice 98:436-444 (2012).
Lu, et al., "Characterization of a Novel Glucokinase Activator in Rat and Mouse Models," PLOS One 9(2):88431 (2014).
Matschinsky, "GKAs for diabetes therapy: why no clinically iseful drug after two decades of trying?," Trends in Pharmacological Sciences, vol. 34, No. 2 (2013).
Migoya et al., "The Glucokinase (GK) Activator MK-0599 Lowers Plasma Glucose Concentrations in Healthy Non-Diabetic Subjects" Abstract (2009).
Pending Claims for U.S. Appl. No. 14/071,976, filed Nov. 5, 2013.
Pending Claims for U.S. Appl. No. 14/840,657, filed Aug. 31, 2015.
Pending Claims for U.S. Appl. No. 14/840,682, file Aug. 31, 2015.
Per Lindstrom, "The Physiology of Obese-Hyperglycemic Mice [ob/ob Mice]," The Scientific World Journal 7:666-685 (2007).
Pfefferkom, "Strategies for the design of hepatoselective glucokinase activators to treat type 2 diabetes," Expert Opin. Drug Discov. 8(3):319-330 (2013).
Valcarce, et al., "TTP399, a Novel, Liver Selective GLucokinase Activator: Results from a 10 day Pilot Study in Patients with type 2 Diabetes Mellitus *(T2DM) Naive to Drug," Poster presented at the 76th Scientific Sessions of the American Diabetes Association in New Orleans, LA, Jun. 11-13, 2016.
Vella, A et al., "TTP399: A liver-selective and Therapeutically Viable Glucokinase Activator . . . Phase 2 Study" presented at the 17th Annual Rachmiel Levine-Arthur Riggs Diabetes Research Symposium, Endocrine Society ENDO2017 Conference, Orlando, Florida, Mar. 27-Apr. 4, 2017.
Vella, A. et al., Abstract "TTP399: A liver-selective and Therapeutically Viable Glucokinase Activator . . . Study" presented at the 17th Annual Rachmiel Levine-Arthur Riggs Diabetes Research Symposium, Endocrine Society ENDO2017 Conference, Orlando, Florida, Mar. 27-Apr. 4, 2017.

* cited by examiner

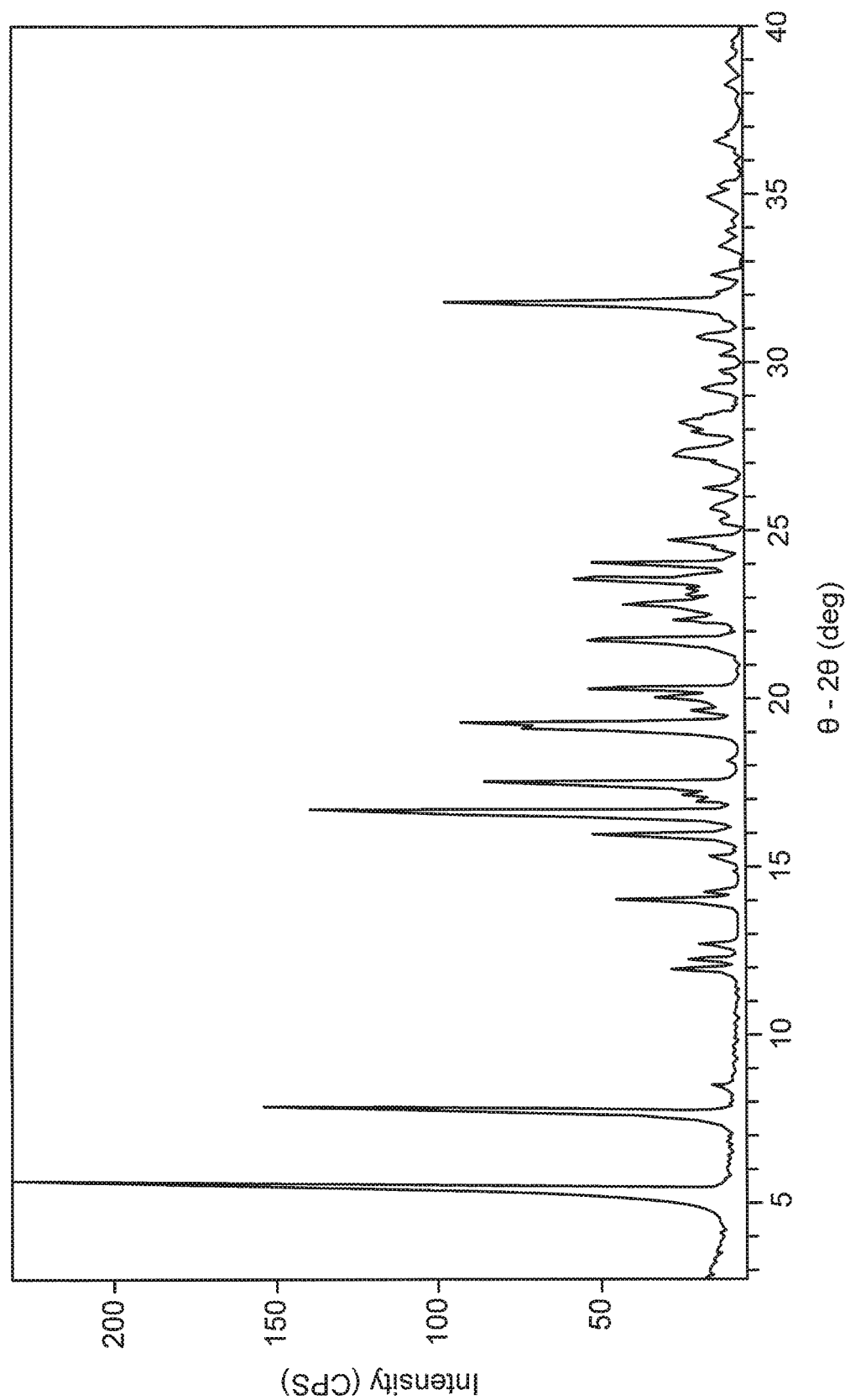

USE OF METFORMIN IN COMBINATION WITH A GLUCOKINASE ACTIVATOR AND COMPOSITIONS COMPRISING METFORMIN AND A GLUCOKINASE ACTIVATOR

BACKGROUND OF THE INVENTION

Diabetes is characterized by impaired glucose metabolism, and manifests itself, among other ways, by elevated blood glucose (BG) levels in untreated diabetic patients. Diabetes is generally known as being one of two types: type 1 diabetes (or insulin-dependent diabetes mellitus), which arises when patients lack insulin-producing β cells in their pancreatic glands; and type 2 diabetes (or non-insulin dependent diabetes mellitus), which arises when patients have impaired β-cell function, in addition to a range of other abnormalities.

Treatment of type 2 diabetes can include the administration of common agents that stimulate β-cell function or that enhance the tissue sensitivity of patients towards insulin. Various agents are known to stimulate β-cell function, including, for example, sulfonylureas, such as tolbutamide, glibenclamide, glipizide, chlorpropamide, and gliclazide, and repaglinide. Other agents are known to enhance tissue sensitivity towards insulin, such as metformin.

Although such common agents are widely used in the treatment of type 2 diabetes, the therapy is often leads to unsatisfactory results. In many patients, such treatments do not normalize BG levels to the desired degree, which places patients at a higher risk of acquiring further diabetic complications. Furthermore, these treatments are known to cause adverse effects in many patients. For example, the sulfonylureas may induce hypoglycemia when taken alone or in combination with other drugs. And while metformin does not induce hypoglycemia to the same degree as sulfonylureas, it has other adverse effects. For example, metformin may cause gastrointestinal distress, where the incidence of such distress may increase with higher doses. Long-term use of metformin can also cause increased homocysteine levels and can lead to malabsorption of vitamin B12. Metformin may also induce production of lactate, which can contribute to lactic acidosis in some patient populations.

In recent years, metformin has been approved for use in combination with other antidiabetic drugs. For example, metformin has been combined with certain sulfonylureas, including glipizide and glibenclamide. Metformin has also been combined with agents that stimulate PPAR-γ receptors, such as pioglitazone and rosiglitazone, and with agents that stimulate the release of insulin from the pancreas, such as repaglinide.

But in any combination therapy, metformin can still exhibit adverse effects, including those described above. Therefore, there is a need to discover agents that, when used with metformin, may exhibit a synergistic effect on glycemic control, thereby allowing a subjects to reduce their daily intake of metformin.

Glucokinase (GK) is an enzyme that, among other things, facilitates phosphorylation of glucose to glucose-6-phosphate. In vertebrates, GK-mediated glucose phosphorylation typically occurs in cells in the liver, pancreas, gut, and brain. In each of these organs, GK can play a role in regulating carbohydrate metabolism by acting as a glucose sensor, triggering shifts in metabolism or cell function in response to rising and/or falling levels of BG.

Small-molecule GK activators are useful in treating type 2 diabetes because they can activate GK, and thereby indirectly reduce the body's demand for insulin. WO 2005/066145 describes novel compounds that are useful as GK activators, and are therefore useful, among other things, for the treatment of type 2 diabetes. Among the disclosed compounds are {2-[3-cyclohexyl-3-(trans-4-propoxy-cyclohexyl)-ureido]-thiazol-5-ylsulfanyl}-acetic acid and pharmaceutically acceptable salts thereof (referred to collectively as "Urea Derivatives 1" or "UD1"). The free acid, {2-[3-cyclohexyl-3-(trans-4-propoxy-cyclohexyl)-ureido]-thiazol-5-ylsulfanyl}-acetic acid, is referred to herein as "UD1-FA".

FIELD OF THE INVENTION

The invention provides for the use of a glucokinase (GK) activator in combination with an antidiabetic drug, such as metformin, for the treatment of type 2 diabetes and other conditions. The invention also provides pharmaceutical compositions comprising a GK activator and an antidiabetic drug, such as metformin.

BRIEF SUMMARY OF THE INVENTION

The invention provides for the use of a glucokinase (GK) activator in combination with metformin for the treatment of type 2 diabetes and related disorders.

In one aspect, the invention provides methods of treating type 2 diabetes by administering to a subject a GK activator in combination with metformin. In some embodiments, the GK activator and metformin are administered simultaneously, either in separate dosage forms or the same dosage form. But in other embodiments, the GK activator and metformin are not necessarily administered simultaneously, but are instead administered according to a sequence. In other embodiments, either the GK activator or metformin is administered subsequent to the other, so that an amount of both are simultaneously present in the subject (as determined, for example, by analysis of the subject's blood or blood plasma).

In another aspect, the invention provides methods of treating type 1 diabetes by administering to a subject a GK activator in combination with metformin. In some embodiments, the GK activator and metformin are administered simultaneously, either in separate dosage forms or the same dosage form. But in other embodiments, the GK activator and metformin are not necessarily administered simultaneously, but are instead administered according to a sequence. In other embodiments, either the GK activator or metformin is administered subsequent to the other, so that an amount of both are simultaneously present in the subject (as determined, for example, by analysis of the subject's blood or blood plasma).

In another aspect, the invention provides methods of lowering blood-glucose in a subject by administering to the subject a GK activator in combination with metformin. In some embodiments, the GK activator and metformin are administered simultaneously, either in separate dosage forms or the same dosage form. But in other embodiments, the GK activator and metformin are not necessarily administered simultaneously, but are instead administered according to a sequence. In other embodiments, either the GK activator or metformin is administered subsequent to the other, so that an amount of both are simultaneously present in the subject (as determined, for example, by analysis of the subject's blood or blood plasma).

In another aspect, the invention provides methods of enhancing phosphorylation of glucose in a subject by administering to the subject a GK activator in combination with metformin. In some embodiments, the GK activator and metformin are administered simultaneously, either in separate dosage forms or the same dosage form. But in other embodiments, the GK activator and metformin are not necessarily administered simultaneously, but are instead administered according to a sequence. In other embodiments, either the GK activator or metformin is administered subsequent to the other, so that an amount of both are simultaneously present in the subject (as determined, for example, by analysis of the subject's blood or blood plasma).

In another aspect, the invention provides methods of improving insulin sensitivity in a subject by administering to the subject a GK activator in combination with metformin. In some embodiments, the GK activator and metformin are administered simultaneously, either in separate dosage forms or the same dosage form. But in other embodiments, the GK activator and metformin are not necessarily administered simultaneously, but are instead administered according to a sequence. In other embodiments, either the GK activator or metformin is administered subsequent to the other, so that an amount of both are simultaneously present in the subject (as determined, for example, by analysis of the subject's blood or blood plasma).

In another aspect, the invention provides pharmaceutical compositions comprising a GK activator and metformin. In some embodiments, the pharmaceutical composition also comprises a pharmaceutically acceptable carrier, excipient, diluent, or a mixture thereof.

In another aspect, the invention provides a metformin salt of a GK activator, and to pharmaceutical compositions comprising said salt. In a further aspect, the provides any of the aforementioned methods, such that the method comprises administering a metformin salt of a GK activator to a subject.

Additional features and aspects of the present invention are described hereinafter.

BRIEF DESCRIPTION OF THE DRAWINGS

FIG. 1 shows a PXRD diffractogram for sample containing a crystalline 1:1 metformin salt of UD1-FA.

DETAILED DESCRIPTION OF THE INVENTION

I. General

In the early stages, patients with type 2 diabetes may exhibit a decreasing ability of their pancreas to secrete sufficient insulin to control post-prandial blood-glucose levels. At first, type 2 diabetics may be able to control progression of the disease by following dietary restrictions, such as consuming foods having a low glycemic index. But as the disease progresses, diet alone is insufficient to control blood-glucose levels. Thus, medical intervention becomes necessary. At this stage (or even in advance of this stage), physicians may prescribe an oral antidiabetic agent to aid in glycemic control. Common oral antidiabetic agents include, for example, sulfonylureas, such as glibenclamide, and biguanides, such as metformin.

These common antidiabetics may have undesirable side-effects in certain patient populations, and may also fail to provide desirable levels of glycemic control. Thus, scientists have continued to search for compounds that can replace or supplement the use of these common antidiabetics. Glucokinase (GK) activators represent one such class of compounds.

GK is an enzyme that, among other things, facilitates phosphorylation of glucose to glucose-6-phosphate. In vertebrates, GK-mediated phosphorylation generally occurs in cells in the liver, pancreas, gut, and brain. In each of these organs, GK can play a role in regulating carbohydrate metabolism by acting as a glucose sensor, triggering shifts in metabolism or cell function in response to rising and/or falling levels of blood-glucose.

Small-molecule GK activators are useful in treating type 2 diabetes because they can enhance the rate of glucose phosphorylation, and thereby reduce the amount of glucose in the blood. Therefore, GK activators lower the body's demand for insulin, especially following intake of food. In this way, GK activators provide an alternate treatment option for type 2 diabetics who otherwise may have difficulty achieving effective glycemic control.

Various GK activators are known. For example, {2-[3-cyclohexyl-3-(trans-4-propoxy-cyclohexyl)-ureido]-thiazol-5-ylsulfanyl}-acetic acid is a GK activator. The preparation and pharmaceutical use of this compound and salts thereof are described in WO 2005/066145.

As described in further detail below, it was discovered that GK activators may exhibit a synergistic effect in lowering blood glucose levels when administered in combination with metformin. Type 2 diabetics often take metformin in large amounts, such as 1000-2500 mg of metformin daily. See Remington's, 21st edition, pp. 1454-55 (2006). It is not expected that metformin will have much of an effect on lowering glucose when administered at smaller doses. Id. at 1455 (noting that certain therapeutic benefits are not generally observed until a subject is administered at least 1000 mg daily of metformin). Because a GK activator and metformin may have a synergistic effect, one can administer to a subject a smaller amount of metformin (e.g., a suboptimal amount) and achieve therapeutic benefits, such as blood-glucose lowering, that would otherwise only have been observed when higher doses (including prohibitively higher doses) of metformin are administered.

Thus, in at least one aspect, the invention provides for the use of a glucokinase (GK) activator in combination with metformin, for the treatment of type 2 diabetes, type 1 diabetes, and other related conditions. Such related conditions include, but are not limited to: metabolic syndrome, glucose intolerance, hyperglycemia, dyslipidemia, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of GK is beneficial, and complications resulting from or associated with diabetes, including, but not limited to, neuropathy, retinopathy, nephropathy, and impaired wound healing.

The invention also relates to pharmaceutical compositions comprising a GK activator and metformin.

II. Pharmaceutical Compositions

In some embodiments of the invention, metformin and/or a GK activator may be included within a pharmaceutical composition. In some such embodiments, a single pharmaceutical composition comprises both metformin and a GK activator. In some further such embodiments, two or more pharmaceutical compositions are provided, where at least one pharmaceutical composition comprises metformin and at least one other pharmaceutical composition comprises a GK activator. As used herein, the term "pharmaceutical composition" refers to a solid composition (e.g., a granulated powder) that contains a pharmaceutically active ingredient (e.g., metformin and/or a GK activator) and at least a carrier, diluent, or excipient, where none of the ingredients is generally biologically undesirable at the administered quantities. In some embodiments, metformin and the GK activator are included in separate pharmaceutical compositions, each of which also includes a pharmaceutically acceptable carrier, diluent, excipient, or mixture thereof. In other embodiments, metformin and the GK activator are included in the same pharmaceutical composition, which also includes a pharmaceutically acceptable carrier, diluent, excipient, or mixture thereof.

As used herein, the term "a mixture of" or "a mixture thereof" refers to any mixture of two or more materials and/or compositions that would be encompassed within the list that follows or precedes the phrase, respectively. The phrase does not refer to any particular type of mixture. Thus, the "mixture" is not necessarily an intimate mixture, a homogeneous mixture, etc. Furthermore, the "mixture" need not contain a representative of each element in the list. For example, if a composition comprises "A, B, C, or a mixture thereof" the term contemplates mixtures of A and B (with no C present), mixtures of B and C (with no A present), mixtures of A and C (with no B present), as well as mixtures of A, B, and C. As a further illustration, suppose that A, B, or C define generic categories (e.g., a polysorbate), where, for example, $A^1$ and $A^2$ are species or subgenuses encompassed by the genus A. In that instance, if a composition comprises "A, B, C, or a mixture thereof," the term also contemplates mixtures of $A^1$ and $A^2$ (where no B and no C are present in the mixture).

Metformin

N,N-dimethylimidodicarbonimidic diamide is often referred to as metformin or 1,1-dimethylbiguanide. Metformin can exist as a free base, or may form salts, including pharmaceutically acceptable salts, such as a hydrochloride salt (e.g., a mono-hydrochloride salt). See Remington's, 21st edition, pp. 1454-55 (2006). As used herein, the term "metformin" is not limited to the free base, but also includes metformin salts, such as pharmaceutically acceptable salts of metformin, hydrochloride salts of metformin, and a mono-hydrochloride salt. As used herein, the term "1,1-dimethylbiguanide" refers only to the free base unless the text expressly indicates that salted forms are also contemplated.

The metformin may be included in any suitable dosage form. For example, metformin may exist in a powder, a tablet, a capsule, and the like. Such dosage forms may, in some embodiments, also include specialized coatings, matrices, and the like to give effect a sustained release, a controlled release, enteric release, etc. In some embodiments, metformin may exist in a dosage form with another therapeutically active ingredient. In some such embodiments, the therapeutically active ingredient is a GK activator. In some embodiments, the therapeutically active ingredient is a liver-selective GK activator. In some embodiments, the therapeutically active ingredient is UD1.

As used throughout this specification, the term "pharmaceutically acceptable salt," refers to salts of a free acid or a free base which are not biologically undesirable and are generally prepared by reacting the free base with a suitable organic or inorganic acid or by reacting the acid with a suitable organic or inorganic base. The term may be used in reference to any compound, including 1,1-dimethylbiguanide, and a GK activator (having a free acid or free base functionality), etc. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present (e.g., in a GK activator), such as —COOH, there can be formed the ammonium, morpholinium, sodium, potassium, barium, calcium salt, and the like, for use as the dosage form. When a basic group is present (e.g., in a GK activator or 1,1-dimethylbiguanide), such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in Stephen M. Berge, et al., Journal of Pharmaceutical Science, Vol. 66(1), pp. 1-19 (1977).

GK Activators

As used herein, a "GK activator" is a compound that activates GK activity in a mammalian subject, such as a human, in direct or indirect response to the presence of the compound, or a metabolite thereof, in the subject. WO 2005/066145 provides a non-limiting list of compounds that are GK activators. In some embodiments, the GK activator is a small molecule, such as a molecule having a molecular weight between 200 amu and 2000 amu, or between 200 amu and 1200 amu, or between 200 amu and 800 amu. Further, GK activators may activate GK wherever GK is present, but some may be selective to certain GK activity in certain systems or organs. For the treatment of type 2 diabetes and related disorders, one is generally concerned with GK activation in the pancreas and/or the liver. In some embodiments, the GK activator is a liver selective GK activator, meaning that the GK activator directly or indirectly increases glucose utilization in the liver at doses that do not induce a substantial increase in insulin secretion by the pancreas in response to glucose (e.g., less than a 25% increase, or less than a 15% increase, or less than a 10% increase, or less than a 5% increase, or less than a 3% increase in insulin secretion by the pancreas in response to glucose). In some embodiments, the GK activator is {2-[3-cyclohexyl-3-(trans-4-propoxy-cyclohexyl)-ureido]-thiazol-5-ylsulfanyl}-acetic acid or a pharmaceutically acceptable salt thereof.

Combination Therapy

In some embodiments of the invention, metformin is administered in combination with a GK activator, or in combination with a liver-selective GK activator, or in combination with UD1. Administration is typically to a subject, such as a human, for the treatment of a disease, disorder, or condition.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of: delaying the progress of a disease, disorder, or condition; controlling a disease, disorder, or condition; delaying the onset of a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In an embodiment, the "subject" is a human. In another embodiment, the "subject" is a human who exhibits one or more symptoms characteristic of a disease, disorder, or condition. In another embodiment, the "subject" is a human who has a disease, disorder, or condition in which GK is involved. The term "subject" does not require one to have any particular status with respect to a hospital, clinic, or research facility (e.g., as an admitted patient, a study participant, or the like).

As used herein, the term "in combination with," when used, for example, in the context of administering a compound in combination with another compound, places no limit on the method, mode, form, etc. of the administration, so long as the administration results in both compounds being simultaneously biologically available to a subject (e.g., present in the blood plasma) at a common point in time.

As noted above, in some embodiments, metformin is administered in combination with a GK activator, or in combination with a liver-selective GK activator, or in combination with UD1. In some such embodiments, metformin and a GK activator are administered simultaneously, for example, via oral administration. For example, metformin and a GK activator are delivered in a common dosage form, where the dosage form comprises both metformin and a GK activator, or a liver-selective GK activator, or UD1. In another example, metformin and a GK activator are delivered in two or more dosage forms that are administered at approximately the same time (e.g., within less than 30 minutes, or within less than 15 minutes, or within less than 10 minutes, or within less than 5 minutes, or within less than 2 minutes of each other), where at least one dosage form comprises metformin and another dosage form comprises a GK activator, or a liver-selective GK activator, or UD1. In further such embodiments, metformin and a GK activator are administered sequentially, preferably via oral administration. For example, metformin or the GK activator can be administered about 30 minutes apart, or about 1 hour apart, or about 2 hours apart, or about 4 hours apart, or about 8 hours apart, or about 12 hours apart, where one metformin is administered earlier than the GK activator, or vice versa. In even further such embodiments, either metformin or the GK activator is administered subsequent to the other, so long as the administration results in both compounds being simultaneously biologically available to a subject (e.g., present in the blood plasma) at a common point in time. For example, one can be administered about 30 minutes after, or about 1 hour after, or about 2 hours after, or about 4 hours after, or about 8 hours after, or about 12 hours after the administration of the other.

Dosage Forms

The pharmaceutical compositions, described herein, can be packaged in a form for oral administration as discrete units (i.e., dosage forms), such as capsules, tablets, sachets, and the like. Preparation of the solid compositions in forms intended for oral administration is within the ability of one skilled in the art, including the selection of pharmaceutically acceptable additional ingredients from the groups listed above in order to provide pharmaceutically elegant and palatable preparations. Such pharmaceutical compositions may be prepared by methods known in the pharmaceutical formulation art, for example, see Remington's Pharmaceutical Sciences, 18th Ed., (Mack Publishing Company, Easton, Pa., 1990).

In some embodiments, administration of metformin in combination with a GK activator can include administration of a dosage form that comprises metformin and a GK activator, or a liver-selective GK activator, or UD1. In some further embodiments, administration of metformin in combination with a GK activator can include administration of two or more dosage forms, where at least one dosage form comprises metformin and another dosage form comprises a GK activator, or a liver-selective GK activator, or UD1.

Dosage Quantities

In embodiments of the invention, an amount of a GK activator, or a liver-selective GK activator, or UD1, is administered to a subject (e.g., a human) in combination with metformin. The amount of the GK activator administered can vary depending on various factors, including but not limited to, the weight of the subject, the nature and/or extent of the subject's disease, etc. In some embodiments, a GK activator, or a liver-selective GK activator, or UD1, is administered to a subject (e.g., a human), in combination with metformin, in an amount that ranges from 10 mg/day to 1000 mg/day, or from 25 mg/day to 800 mg/day, or from 37 mg/day to 750 mg/day, or from 75 mg/day to 700 mg/day, or from 100 mg/day to 600 mg/day, or from 150 mg/day to 500 mg/day, or from 200 mg/day to 400 mg/day. In some further embodiments, a GK activator, or a liver-selective GK activator, or UD1, is administered to a subject (e.g., a human), in combination with metformin, in an amount of about 100 mg/day, or about 200 mg/day, or about 300 mg/day, or about 400 mg/day, or about 500 mg/day. In even some further embodiments, a GK activator, or a liver-selective GK activator, or UD1, is administered to a subject (e.g., a human), in combination with metformin, in a therapeutically effective amount. As used herein, the term "therapeutically effective amount" refers to an amount of an active ingredient (e.g., GK activator, or a liver-selective GK activator, or UD1) that elicits the biological or medicinal response in a tissue, system, or subject that is being sought by a researcher, veterinarian, medical doctor, patient or other clinician, which includes reduction or alleviation of the symptoms of the disease being treated.

As a monotherapy, metformin may be administered to human subjects in amounts between 1000 mg/day and 2500 mg/day. See Remington's, 21st edition, pp. 1454-55 (2006). In smaller doses, metformin may offer negligible therapeutic benefits when administered as a monotherapy. Id. at 1455. In embodiments of the invention, a GK activator, or a liver-selective GK activator, or UD1, is administered to a subject (e.g., a human) in combination with an amount of metformin. In some embodiments, the amount of metformin administered to a subject (e.g., a human) ranges from 250 mg/day to 2500 mg/day, or from 500 mg/day to 1500 mg/day, or from 250 mg/day to 1000 mg/day, or from 350 mg/day to 850 mg/day, or from 400 mg/day to 750 mg/day. In some further embodiments, the amount of metformin administered to a subject (e.g., a human) is about 250 mg/day, or about 350 mg/day, or about 500 mg/day, or about 600 mg/day, or about 700 mg/day, or about 750 mg/day, or about 850 mg/day, or about 1000 mg/day, or about 1200 mg/day, or about 1500 mg/day, or about 2000 mg/day, or about 2500 mg/day. In some further embodiments, the amount of metformin administered to a subject (e.g., a human) is a therapeutically effective amount.

In some embodiments of the invention, a GK activator, or a liver-selective GK activator, or UD1, is administered to a subject (e.g., a human) in combination with a suboptimal amount of metformin. As used herein in reference to metformin, a "suboptimal amount" is an amount that is less than a therapeutically effective amount as a monotherapy in a typical subject (e.g., a human subject, or a human subject who suffers from type 2 diabetes or type 1 diabetes, or a human subject in need of glycemic control). In some such embodiments, the suboptimal amount of metformin is an amount that ranges from 0.01 mg/day to 1000 mg/day, or from 10 mg/day to about 850 mg/day, or from 37 mg/day to 750 mg/day, or from 50 mg/day to 700 mg/day, or from 75 mg/day to 600 mg/day, or from 100 mg/day to 500 mg/day.

III. Methods of Treatment

In another aspect, the invention provides methods of treating type 2 diabetes by administering to a subject a GK activator, or a liver-selective GK activator, or UD1, in combination with metformin, according to any of the embodiments described in the foregoing sections.

In some embodiments, the invention provides methods of treating type 2 diabetes by administering to a subject a glucokinase activator in combination with a suboptimal amount of metformin. In some embodiments, the glucokinase activator is a liver-selective glucokinase activator. In some embodiments, the glucokinase activator is {2-[3-cyclohexyl-3-(trans-4-propoxy-cyclohexyl)-ureido]-thiazol-5-ylsulfanyl}-acetic acid or a pharmaceutically acceptable salt thereof. In some embodiments, the glucokinase activator and the suboptimal amount of metformin are administered to the subject simultaneously. In some embodiments, the glucokinase activator and the suboptimal amount of metformin are administered, such that one is administered subsequent to the other.

In another aspect, the invention provides methods of treating type 1 diabetes by administering to a subject a GK activator, or a liver-selective GK activator, or UD1, in combination with metformin, according to any of the embodiments described in the foregoing sections.

In another aspect, the invention provides methods of lowering blood-glucose in a subject by administering to the subject a GK activator, or a liver-selective GK activator, or UD1, in combination with metformin, according to any of the embodiments described in the foregoing sections.

In some embodiments, the invention provides methods of lowering blood glucose in a subject by administering to the subject a glucokinase activator in combination with a suboptimal amount of metformin. In some embodiments, the glucokinase activator is a liver-selective glucokinase activator. In some embodiments, the glucokinase activator is {2-[3-cyclohexyl-3-(trans-4-propoxy-cyclohexyl)-ureido]-thiazol-5-ylsulfanyl}-acetic acid or a pharmaceutically acceptable salt thereof. In some embodiments, the glucokinase activator and the suboptimal amount of metformin are administered to the subject simultaneously. In some embodiments, the glucokinase activator and the suboptimal amount of metformin are administered, such that one is administered subsequent to the other.

In another aspect, the invention provides methods of enhancing phosphorylation of glucose in a subject by administering to the subject a GK activator, or a liver-selective GK activator, or UD1, in combination with metformin, according to any of the embodiments described in the foregoing sections.

In some embodiments, the invention provides methods of enhancing phosphorylation of glucose in a subject by administering to the subject a glucokinase activator in combination with a suboptimal amount of metformin. In some embodiments, the glucokinase activator is a liver-selective glucokinase activator. In some embodiments, the glucokinase activator is {2-[3-cyclohexyl-3-(trans-4-propoxy-cyclohexyl)-ureido]-thiazol-5-ylsulfanyl}-acetic acid or a pharmaceutically acceptable salt thereof. In some embodiments, the glucokinase activator and the suboptimal amount of metformin are administered to the subject simultaneously. In some embodiments, the glucokinase activator and the suboptimal amount of metformin are administered, such that one is administered subsequent to the other.

In another aspect, the invention provides methods of improving insulin sensitivity in a subject by administering to the subject a GK activator, or a liver-selective GK activator, or UD1, in combination with metformin, according to any of the embodiments described in the foregoing sections.

In some embodiments, the invention provides methods of improving insulin sensitivity in a subject by administering to the subject a glucokinase activator in combination with a suboptimal amount of metformin. In some embodiments, the glucokinase activator is a liver-selective glucokinase activator. In some embodiments, the glucokinase activator is {2-[3-cyclohexyl-3-(trans-4-propoxy-cyclohexyl)-ureido]-thiazol-5-ylsulfanyl}-acetic acid or a pharmaceutically acceptable salt thereof. In some embodiments, the glucokinase activator and the suboptimal amount of metformin are administered to the subject simultaneously. In some embodiments, the glucokinase activator and the suboptimal amount of metformin are administered, such that one is administered subsequent to the other.

In another aspect, the invention provides methods of boosting or enhancing the therapeutic effectiveness (in terms of enhanced glucose-lowering effect) of metformin by administering to a subject a GK activator, or a liver-selective GK activator, or UD1, in combination with metformin, according to any of the embodiments described in the foregoing sections.

In some embodiments, the invention provides methods of enhancing the therapeutic effectiveness of metformin by administering to the subject a glucokinase activator in combination with metformin. In some embodiments, the glucokinase activator is a liver-selective glucokinase activator. In some embodiments, the glucokinase activator is {2-[3-cyclohexyl-3-(trans-4-propoxy-cyclohexyl)-ureido]-thiazol-5-ylsulfanyl}-acetic acid or a pharmaceutically acceptable salt thereof. In some embodiments, the glucokinase activator and the suboptimal amount of metformin are administered to the subject simultaneously. In some embodiments, the glucokinase activator and the suboptimal amount of metformin are administered, such that one is administered subsequent to the other. In some embodiments, the metformin is administered as a suboptimal amount of metformin.

In another aspect, the invention provides methods of treating a condition comprising administering to a subject a GK activator, or a liver-selective GK activator, or UD1, in combination with metformin, according to any of the embodiments described in the foregoing sections, wherein the condition is selected from metabolic syndrome, glucose intolerance, hyperglycemia, dyslipidemia, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of GK is beneficial, or complications resulting from or associated with diabetes, including, but not limited to, neuropathy, retinopathy, nephropathy, and impaired wound healing.

IV. Pharmaceutical Compositions Containing Metformin and a GK Activator

In a further aspect of the invention, a GK activator, or a liver-selective GK activator, or UD1, can be included in a pharmaceutical composition with metformin. In some embodiments, the GK activator and the metformin are intermixed, optionally in the presence of at least one other pharmaceutically acceptable carrier, diluent, or excipient, such that the GK activator and metformin are homogeneously distributed throughout the composition. In other embodiments, a pharmaceutical composition comprises both a GK activator and metformin, and optionally at least one other pharmaceutically acceptable carrier, diluent, or excipient, where the GK activator and the metformin are not homogeneously distributed throughout the composition.

In some embodiments, the invention provides a pharmaceutical composition of a glucokinase activator, a suboptimal amount of metformin, and at least one pharmaceutically acceptable carrier, excipient, diluent, or a mixture thereof. In some embodiments, the glucokinase activator is a liver-selective glucokinase activator. In some embodiments, the glucokinase activator is {2-[3-cyclohexyl-3-(trans-4-propoxy-cyclohexyl)-ureido]-thiazol-5-ylsulfanyl}-acetic acid or a pharmaceutically acceptable salt thereof. In some embodiments, the glucokinase activator and metformin are distributed homogeneously throughout the pharmaceutical composition. In some embodiments, the glucokinase activator and metformin are not distributed homogeneously throughout the pharmaceutical composition.

As a non-limiting example, the composition may be a solid composition that comprises a bi-layered granule, where one layer in the granule is enriched in a GK activator and the other layer in the granule is enriched in metformin. In some embodiments, the pharmaceutical composition includes granules that each include a glucokinase activator and metformin. Such granules can be made by any suitable granulation method known in the art, including but not limited to, various dry granulation and wet granulation techniques. Furthermore, the particle size and the distribution of particle sizes of the granules can be adjusted according to known techniques to achieve release profiles, dissolution, and the like. In some embodiments, the invention provides a pharmaceutical composition that comprises granules that each comprises a GK activator and metformin. In some such embodiments, at least 80%, or at least 85%, or at least 90%, or at least 95% (by weight) of said granules have a particle size that is between 1 µm and 1 mm. Further, in some such embodiments, at least 80%, or at least 85%, or at least 90%, or at least 95% (by weight) of said granules have a particle size that is between 1 µm and 500 µm.

The granules can be homogeneous or heterogeneous. Homogeneous granules can have an equal distribution of one of or both the glucokinase activator and metformin, throughout each granule. Alternatively, the granules can be heterogeneous, such that some portions of each granule have a higher concentration of glucokinase activator than other portions. The higher concentration of the glucokinase activator and/or the metformin can be achieved in a variety of methods, such as, for example, via layers. The granules can include one or more layers, where each layer can include the glucokinase activator or the metformin, or a combination of the two. For example, one layer can include the glucokinase activator, and another layer the metformin. Alternatively, one layer can include the glucokinase activator in combination with the metformin at one concentration, and a second layer of both the glucokinase activator and metformin at a second concentration.

In some embodiments, at least a portion of the granules have a composition such that the glucokinase activator and the metformin are distributed homogeneously throughout each granule with that portion. In some embodiments, at least a portion of the granules have a composition such that each granule in that portion has at least two layers, wherein one layer is enriched in the glucokinase activator and the other layer is enriched in metformin.

In any embodiment where metformin and/or a GK activator are included in a pharmaceutical composition, such pharmaceutical compositions may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Metformin Salts

In another aspect, the invention provides a salt between a GK activator and metformin, where the GK activator has at least one acidic group, such as, for example, a —$CO_2H$ group. In some such embodiments, the GK activator is a liver-selective GK activator, or UD1. In general, the stoichiometric ratio between metformin and the GK activator is 1:1. The invention does not require any particular amount of the salt to be present; a single pairing between a GK activator ion and a metformin counterion is sufficient. Larger quantities of the salt can be present, however. For example, in some embodiments, at least 5%, or at least 10%, or at least 20%, or at least 40%, or at least 60%, or at least 80%, or at least 90%, or at least 95% of the GK activator (e.g., UD1) is present in a composition as a salt with metformin (based on the total number of moles of said GK activator (e.g., UD1) present in the composition). In some further embodiments, at least 5%, or at least 10%, or at least 20%, or at least 40%, or at least 60%, or at least 80%, or at least 90%, or at least 95% of the metformin is present in a composition as a salt with a GK activator (e.g., UD1) (based on the total number of moles of metformin present in the composition). The salts between a GK activator and metformin need not have any particular crystalline structure or degree of crystallinity. The preparation of such salts is described in the examples below.

In some embodiments, the invention provides a pharmaceutical composition comprising a metformin salt of a GK activator, or a liver-selective GK activator, or UD1, and further comprising a pharmaceutically acceptable carrier, diluent, or excipient, or mixtures thereof. In some such embodiments, the pharmaceutical composition may also comprise additional quantities of metformin and/or a GK activator (e.g., a liver selective GK activator or UD1).

In some embodiments, the invention provides a salt of one molecular cation and one molecular anion, where the molecular cation is a cation of 1,1,-dimethylbiguanide and the molecular anion is an anion of a glucokinase activator. In some embodiments, the glucokinase activator is a liver-selective glucokinase activator. In some embodiments, the glucokinase activator is {2-[3-cyclohexyl-3-(trans-4-propoxy-cyclohexyl)-ureido]-thiazol-5-ylsulfanyl}-acetic acid. In some embodiments, the invention provides a pharmaceutical composition of the salt described above and at least a pharmaceutically acceptable carrier, excipient, diluent, or a mixture thereof.

In any of the aforementioned methods of treatment, administration of metformin and a GK activator may be carries out, in whole or in part, by administering a metformin salt of a GK activator.

V. Examples

Example 1: Treatment of Diabetic ob/ob Mice with UD1 and Metformin

Before treatment, the mice were assigned to four groups based on baseline glucose levels and body weight (n=10 for each group). Each group of mice was dosed with one of the following: (1) a control substance; (2) 75 mg/kg UD1; (3) 100 mg/kg metformin (Met); or (4) 75 mg/kg UD1 and 100 mg/kg metformin (Met). Post-prandial glucose was measured at time points of 1, 3, 5, 7, and 9 hours following dosing. Table 1 shows the mean glucose levels (in mg/dL) for each group at the recited time points. (The standard deviations for the 10 measurements were generally less than 10-15% the mean measured BG level.) The last row of Table 1 shows the change in glucose levels (in terms of glucose lowering) for each group (relative to control) over the course of the 9 hours, measured as AUC for 0-9 hours (in hours-mg/dL).

TABLE 1

| Time (hours) | Control (mg/dL) | UD1 (mg/dL) | Met (mg/dL) | Met + UD1 (mg/dL) |
|---|---|---|---|---|
| 0 | 388 | 391 | 389 | 393 |
| 1 | 433 | 321 | 357 | 213 |
| 3 | 366 | 254 | 334 | 115 |
| 5 | 461 | 376 | 459 | 171 |
| 7 | 447 | 382 | 501 | 222 |
| 9 | 452 | 394 | 484 | 285 |

| | Control (h-mg/dL) | UD1 (h-mg/dL) | Met (h-mg/dL) | Met + UD1 (h-mg/dL) |
|---|---|---|---|---|
| AUC 0-9 hrs | 0 | −748 | −39 | −2027 |

As is evident from the AUC for 0-9 hours, the combination therapy of the GK activator (UD1) with a sub-optimal amount of metformin led to a glucose-lowering effect that is in excess of a simply additive glucose-lowering effect. Thus, the results show a synergistic benefit in ob/ob mice in terms of glucose lowering for the combination of UD1 and a sub-optimal amount of metformin.

Example 2 Preparation of a Metformin Salt of UD1

NaOH (0.8 g) was dissolved in water (20 mL) and then cooled to room temperature. 1,1-dimethylbiguanide hydrochloride (3.6 g) was then added and stirred to obtain a clear solution. The resulting solution was added to a suspension of {2-[3-cyclohexyl-3-(trans-4-propoxy-cyclohexyl)-ureido]-thiazol-5-ylsulfanyl}-acetic acid (UD1) (9.1 g) in ethanol (80 mL) with stirring at room temperature. The reaction mixture turned clear in 3-5 minutes. The volatiles were evaporated to obtain a syrup, which was dissolved in ethanol (100 mL) and then concentrated. White precipitate was obtained when about 50 mL of volatiles were removed by evaporation. This precipitate was filtered and dried under reduced pressure to obtain a 1,1-dimethylbiguanide salt of {2-[3-cyclohexyl-3-(trans-4-propoxy-cyclohexyl)-ureido]-thiazol-5-ylsulfanyl}-acetic acid. The $^1$H NMR spectrum recorded in DMSO-$d_6$ indicated the precipitate contained {2-[3-cyclohexyl-3-(trans-4-propoxy-cyclohexyl)-ureido]-thiazol-5-ylsulfanyl}-acetic acid and 1,1-dimethylbiguanide in 1:1 ratio. $^1$H NMR (400 MHz, DMSO-$d_6$): δ 0.85 (t, 3H), 1.05-2.15 (m, 20H), 2.92 (s, 6H), 3.18 (m, 1H), 3.30 (s, 2H), 3.34 (t, 2H), 3.45 (br, 1H), 7.1 (br, NH protons), 7.21 (s, 1H) ppm.

Example 3 PXRD of a Metformin Salt of UD1

FIG. 1 shows the PXRD diffractogram for a sample containing a crystalline 1:1 salt of metformin and UD1-FA. The data were collected using a PANalytical X'Pert Prop diffractometer using Cu-Kα incident radiation using an Optix long, fine-focus source. Data were collected and analyzed using X'Pert Pro Data Collector software (v. 2.2b). Prior to analysis, calibration was carried out using the Si 111 peak position. The physical specimen was sandwiched between 3-μm-thick films, analyzed in transmission geometry, and rotated to optimize orientation statistics. A beamstop was used. The diffraction pattern was collected using a scanning position-sensitive detector (X'Celerator) located 240 mm from the specimen.

Example 4A

A metformin salt of UD1-FA was prepared, as described above, and suspended in water. For comparison, two solid formulations of UD1 were prepared: a capsule (Example 4B) and a tablet (Example 4C).

Example 4B 57.6 g of TWEEN 80 and 14.4 g of HPMC E3 LV were dissolved in 1100 mL of water. 1600.0 g of UD1-FA, 280.0 g of AVICEL PH101, 299.2 g of lactose monohydrate, and 184.0 g of AC-DI-SOL were transferred to a high shear granulator. The powder was blended for 2 minutes at 250 rpm with the chopper off. The HPMC/TWEEN 80 solution was then pumped into the granulator while mixing for 1-2 minutes with an impeller speed of 250 rpm and chopper speed of 1000 rpm. Additional water was added to complete the granulation. The wet granules were transferred to a Vector FL-Multi-3 Fluid bed drier and dried the granules to LOD of <3.0% using inlet temperature of 50-60° C. The dried granules were passed through a #30 mesh screen. 2189.4 g of the wet granulation were thoroughly blended with 128.02 g of AVICEL PH101, 129.46 g of AC-DI-SOL, 129.46 g of pregelatinized starch (Starch 1500), and 12.95 g of magnesium stearate. The resulting mixture was then filled in Swedish orange opaque capsules using encapsulator equipment. Each capsule weighed 360 mg and contained 200 mg of UD1-FA.

Example 4C 12.14 g of UD1-FA, 1.08 g of TWEEN 80, and 0.08 g of HPMCAS were dissolved in 485 mL of THF. The solution was spray dried onto a mixture of 7.20 g of AVICEL PH101, 7.20 g of lactose DT, and 3.0 g of crospovidone using fluidized bed granulation (Vector Laboratory Micro Fluid Bed) equipment. The granules were passed through a #60 mesh screen to obtain a mixture of fine powder and small granules. 2.55 g of this powder was thoroughly blended with 0.23 g of AVICEL PH101, 0.16 g of crospovidone, 0.38 g of corn starch, 0.05 g of CAB-O-SIL, 0.14 g of sodium lauryl sulfate, 1.50 g of anhydrous sodium carbonate, 0.50 g of anhydrous sodium bicarbonate, and 0.03 g of magnesium stearate. The resulting mixture was compressed into tablets using SC-2 single station tablet press from Key International; each tablet had hardness of 8-12 Kp. Each tablet weighed 555 mg and contained 100 mg of UD1-FA.

Example 4D

The three dosage forms (the salt in water, the capsule, and the tablet) were each administered to three male beagle dogs. For all nine dogs, 100 mg of UD1 was administered orally. Each dog was dosed in a fasted state, where food was provided 4 hours following dosing. Blood samples were taken for pharmacokinetic (PK) evaluation at the following time intervals following dosing: 0.5, 1.0, 2.0, 4.0, 6.0, 8.0, 12.0, and 24.0 hours. Table 2, below, shows the mean results for various PK parameters for the three groups of dogs.

TABLE 2

|  | Metformin Salt | Capsule | Tablet |
| --- | --- | --- | --- |
| Dose (mg/kg) | 9.3 | 10.4 | 9.8 |
| $C_{max}$ (ng/mL) | 6985 | 4127 | 6500 |
| $t_{1/2}$ (hours) | 2.85 | 3.01 | 2.41 |
| $AUC_{0-\infty}$ (h · ng/mL) | 15802 | 11843 | 14820 |

The metformin salt of UD1 showed improved PK parameters over the capsule and even over the tablet that had included carbonate and bicarbonate.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of lowering blood glucose in a subject comprising:
   administering to the subject {2-[3-cyclohexyl-3-(trans-4-propoxy-cyclohexyl)-ureido]-thiazol-5-ylsulfanyl}-acetic acid or a pharmaceutically acceptable salt thereof in combination with metformin, wherein the metformin is administered in an amount of less than 1000 mg/day.

2. The method of claim 1, wherein the metformin is administered in an amount between 0.01 mg/day and less than 1000 mg/day.

3. The method of claim 1, wherein the metformin is administered in an amount between 10 mg/day and 850 mg/day.

4. The method of claim 1, wherein the metformin is administered in an amount between 10 mg/day and less than 1000 mg/day.

5. The method of claim 1, wherein {2-[3-cyclohexyl-3-(trans-4-propoxy-cyclohexyl)-ureido]-thiazol-5-ylsulfanyl}-acetic acid is administered in an amount of less than 1000 mg/day.

6. The method of claim 1, wherein the metformin is 1,1-dimethylbiguanide monohydrochloride.

7. The method of claim 2, wherein the metformin is 1,1-dimethylbiguanide monohydrochloride.

8. The method of claim 3, wherein the metformin is 1,1-dimethylbiguanide monohydrochloride.

9. The method of claim 4, wherein the metformin is 1,1-dimethylbiguanide monohydrochloride.

10. The method of claim 5, wherein the metformin is 1,1-dimethylbiguanide monohydrochloride.

11. The method of claim 1, wherein the subject is a human.

12. The method of claim 11, wherein the subject is suffering from type 2 diabetes.

13. The method of claim 1, wherein the {1-[3-cyclohexyl-3-(trans-4-propoxy-cyclohexyl)-ureido]-thiazol-5-ylsulfanyl}-acetic acid or a pharmaceutically acceptable salt thereof and the metformin are administered in the same dosage form.

14. The method of claim 1, wherein the {1-[3-cyclohexyl-3-(trans-4-propoxy-cyclohexyl)-ureido]-thiazol-5-ylsulfanyl}-acetic acid or a pharmaceutically acceptable salt thereof and the metformin are administered in separate dosage forms.

15. The method of claim 1, wherein the {1-[3-cyclohexyl-3-(trans-4-propoxy-cyclohexyl)-ureido]-thiazol-5-ylsulfanyl}-acetic acid or a pharmaceutically acceptable salt thereof and the metformin are administered simultaneously.

16. The method of claim 1, wherein the {2-[3-cyclohexyl-3-(trans-4-propoxy-cyclohexyl)-ureido]-thiazol-5-ylsulfanyl}-acetic acid or a pharmaceutically acceptable salt thereof and the metformin are administered in sequence so that a synergistically effective amount of both are simultaneously present in the subject.

* * * * *